(12) United States Patent
Squicciarini

(10) Patent No.: US 9,968,807 B2
(45) Date of Patent: May 15, 2018

(54) SEALED AND VENTILATED RECEPTACLE

(71) Applicant: Robert Squicciarini, Farmingdale, NY (US)

(72) Inventor: Robert Squicciarini, Farmingdale, NY (US)

( * ) Notice: Subject to any disclaimer, the term of this patent is extended or adjusted under 35 U.S.C. 154(b) by 989 days.

(21) Appl. No.: 14/145,063

(22) Filed: Dec. 31, 2013

(65) Prior Publication Data
US 2014/0182160 A1    Jul. 3, 2014

Related U.S. Application Data

(60) Provisional application No. 61/748,180, filed on Jan. 2, 2013.

(51) Int. Cl.
*A62B 15/00* (2006.01)
*B08B 15/02* (2006.01)
*A61L 2/10* (2006.01)

(52) U.S. Cl.
CPC ............ *A62B 15/00* (2013.01); *B08B 15/023* (2013.01); *A61L 2/10* (2013.01); *A61L 2202/14* (2013.01)

(58) Field of Classification Search
CPC ....... D06F 58/10; A62B 15/00; B08B 15/023; A61L 2/10; A61L 2202/14
See application file for complete search history.

(56) References Cited

U.S. PATENT DOCUMENTS

| | | | | |
|---|---|---|---|---|
| 4,995,516 A * | 2/1991 | Fine | ..................... | A47B 61/003 211/85.3 |
| 5,178,581 A * | 1/1993 | Del Monte | ............... | F24F 7/08 454/239 |
| 5,185,939 A * | 2/1993 | Kimura | .................. | A43D 95/10 34/105 |
| 5,815,961 A * | 10/1998 | Estes | ....................... | D06F 73/02 223/67 |
| 6,868,621 B1 * | 3/2005 | Grimm | ................... | D06F 58/10 34/104 |
| 2006/0113061 A1 * | 6/2006 | Ronnlund | .......... | B60H 1/00378 165/43 |
| 2007/0193058 A1 * | 8/2007 | Zarembinski | .......... | D06F 58/10 34/202 |

* cited by examiner

*Primary Examiner* — Jessica Yuen
(74) *Attorney, Agent, or Firm* — Thomas A. O'Rourke; Bodner & O'Rourke, LLP

(57) ABSTRACT

The present invention relates to a sealed and ventilated receptacle for storing equipment, such as firefighter turnout gear, that generally includes a base, at least one sidewall extending from the base, and a top wall that covers the opposite end of the sidewall. A sealable door may be positioned on the sidewall to access the inside of the receptacle and to prevent any contaminants from exiting the receptacle. The receptacle may also include an intake fan and exhaust fan that are each connected to a duct for providing fresh air to and removing contaminated air from the inside of the receptacle. The receptacle may further include a temperature control unit for regulating the temperature inside of the receptacle. Additionally, a hook for hanging a firefighter coat, trousers, or other items may also be included on the inside of the receptacle.

16 Claims, 6 Drawing Sheets

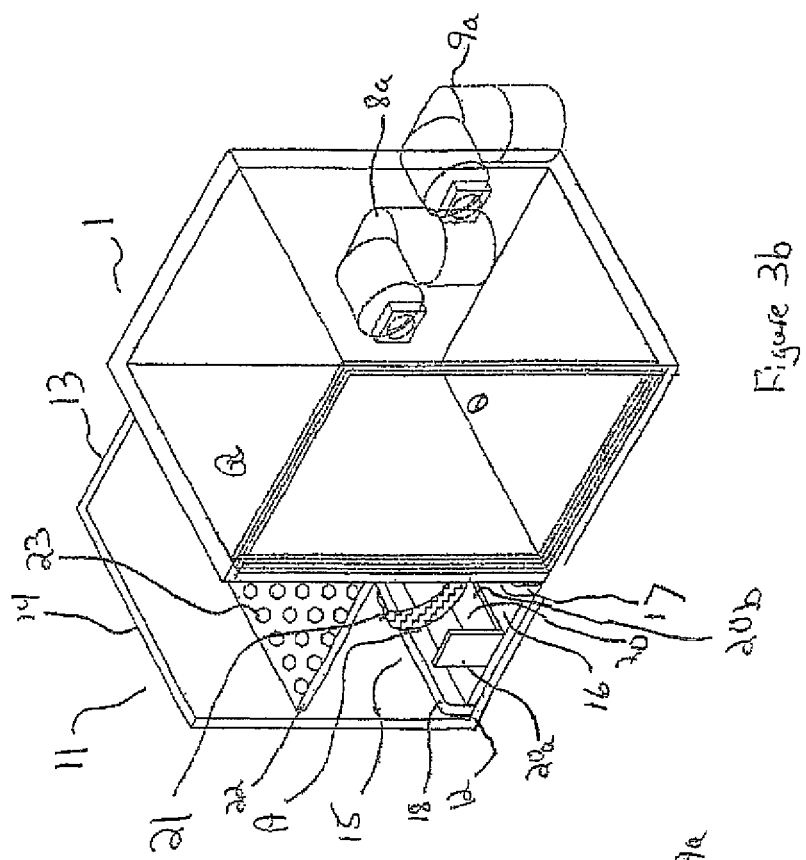
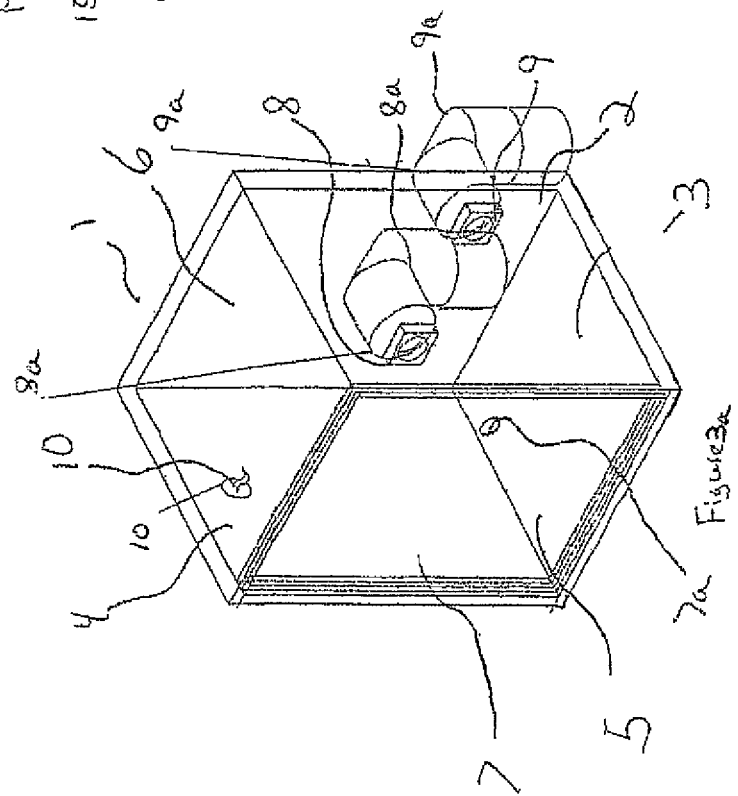

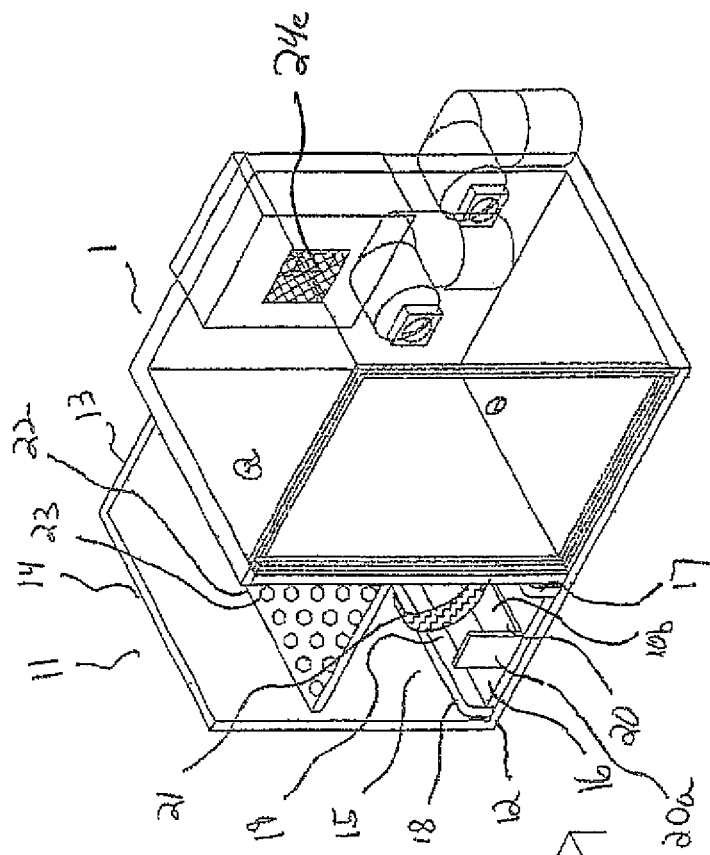
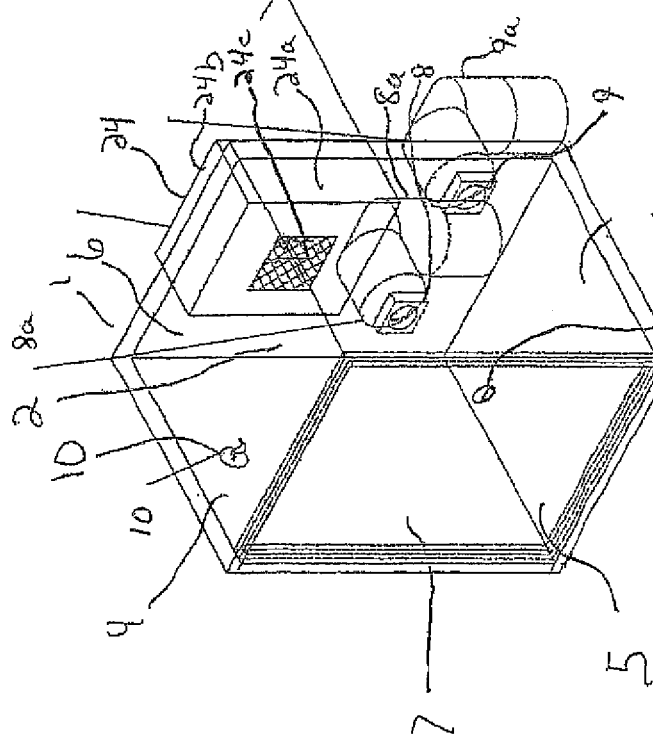
Figure 6b
Figure 6a

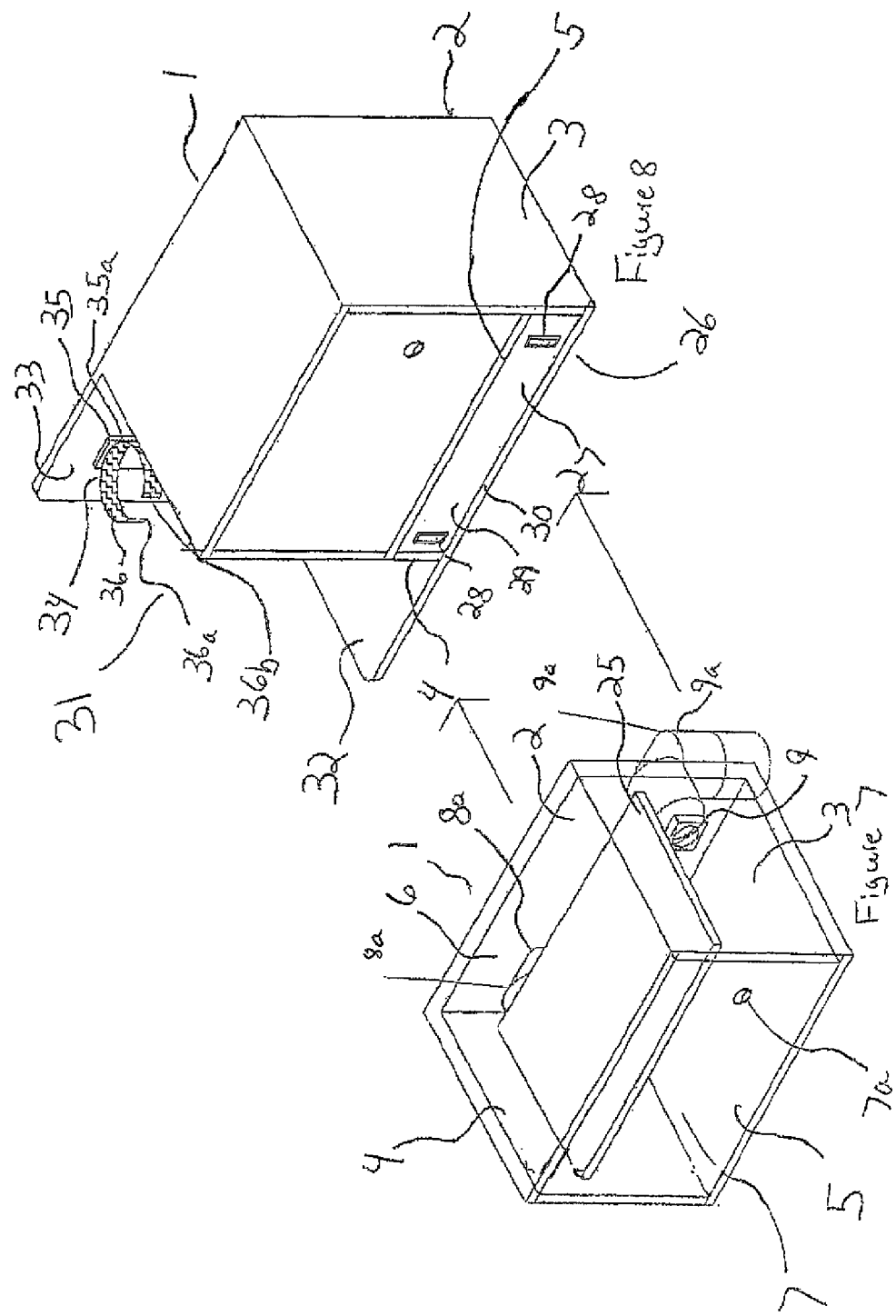

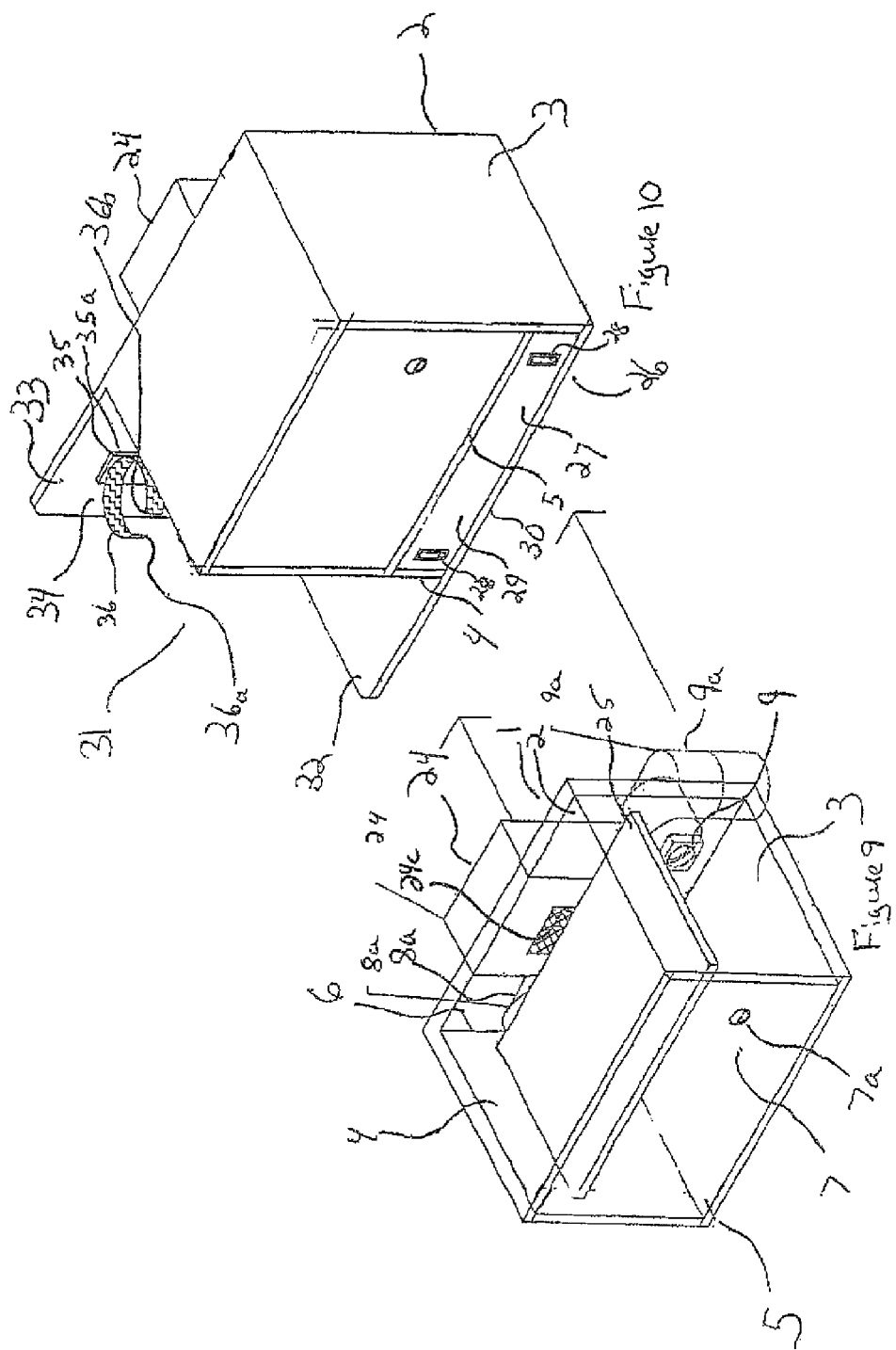

SEALED AND VENTILATED RECEPTACLE

FIELD OF THE INVENTION

The present invention relates to sealed receptacles that are ventilated for storing equipment. More specifically, the present invention relates to a receptacle for storing firefighter turnout gear or other items that require a sealed and ventilated chamber.

BACKGROUND OF THE INVENTION

The term "turnout gear" refers to the system of outer protective clothing that is worn by firefighters before entering a hazardous environment. The turnout gear generally consists of fire resistant boots, fire resistant trousers, fire resistant coat, fire resistant gloves, the firefighter nomex head hood, and the firefighter helmet. Firefighters typically carry their personal turnout gear in their vehicles, such as in the trunk of a sports utility vehicle ("SUV"), so that they will be ready to respond to an emergency. The gear is stored in specially manufactured cabinets that are designed to accommodate the different components of the gear. However, since the turnout gear is exposed to the smoke and contaminants that are present in the hazardous environments that firefighters respond to, the Federal National Fire Protection Association ("NFPA") has passed regulations that require the turnout gear to be stored in a special fashion.

Relevant provisions of the regulations include section 9.1.1 which states that the firefighter turnout gear "shall not be stored in direct sunlight or exposed to direct sunlight while not being worn." Section 9.1.4 states that the gear "shall not be stored at temperatures below −32° C. (−25° F.) or above 82° C. (180° F.)." Section 9.1.6 requires that the gear shall only be stored in living quarters, with personal belongings, or taken or transported in the passenger compartment of personal vehicles if the gear is "placed in a protective case or bag to prevent cross contamination." Section 9.1.8 requires the "firefighter protective coat and trouser elements [to] be stored by hanging".

As a result of the NFPA's regulations, there is a need in the art for cabinets that comply with the regulations to allow firefighters to continue to carry their personal turnout gear in their vehicles. The present invention discloses cabinets that contain a specially designed receptacle that is sealed and ventilated in order to allow firefighters to continue to store their gear in the trunk of their car or other desired location.

OBJECTS OF THE INVENTION

It is an object of the invention to provide a receptacle for storing firefighter turnout gear that complies with the NFPA storage requirements.

It is another object of the invention to provide a receptacle or a cabinet that contains the receptacle of the invention for storing firefighter turnout gear in the trunk of a vehicle.

It is a further object of the invention to provide a receptacle for storing firefighter turnout gear that is easy and convenient to use.

It is still a farther object of the invention to provide a receptacle for storing firefighter turnout gear that includes intake and exhaust means for ventilating the receptacle.

It is an even further object of the invention to provide a receptacle for storing firefighter turnout gear that includes a door that seals the enclosure of the receptacle.

It is still an even further object of the invention to provide a receptacle that includes a temperature control unit for maintaining the temperature inside of the receptacle.

SUMMARY OF THE INVENTION

The present invention is directed to a receptacle for preferably storing firefighter turnout gear inside of a vehicle, such as a sports utility vehicle ("SUV") or a fire engine, that complies with the NFPA regulations. The receptacle is preferably ventilated and sealed and generally includes a base, at least one sidewall extending from the base, and a top wall that covers the opposite end of the sidewall. A sealable door may be positioned on the sidewall to access the inside of the receptacle and to prevent any contaminants from exiting the receptacle. Ventilation means for providing fresh air to and removing stale air from the inside of the receptacle may also be included as well as a temperature control unit to regulate the climate inside of the receptacle. A hanging means, such as a hook, may be placed inside of the receptacle to allow a user to hang an item, such as the firefighter protective coat and/or trousers. In addition, the receptacle may include further storage means, such as having at least one shelf disposed inside of the receptacle and/or having more than one hook on any of the walls and/or shelves of the receptacle for hanging items therein.

Generally, firefighters store their personal turnout gear in the trunk of their vehicle in specially designed cabinets. However, these cabinets do not include the receptacle of the present invention that allows firefighters to store their turnout gear in compliance with NFPA regulations. The receptacle of the present invention is adapted to be used with the specially designed cabinets to allow firefighters to store their personal turnout gear in the trunk of a vehicle or in any other desired location.

BRIEF DESCRIPTION OF THE DRAWINGS

FIG. 3a is a view of the receptacle of FIG. 1.

FIG. 3b is a front view of a cabinet that includes the receptacle of FIG. 3a.

FIG. 6a is a view of the receptacle of FIG. 4.

FIG. 6b is a front view of a cabinet that includes the receptacle of FIG. 6a.

FIG. 7 is a front transparent view of a further alternate embodiment of the receptacle.

FIG. 8 is a front perspective view of a cabinet that includes the receptacle of FIG. 7.

FIG. 9 is a front transparent view of an even further alternate embodiment of the receptacle.

FIG. 10 is a front view of a cabinet that includes the receptacle of FIG. 9.

DETAILED DESCRIPTION OF THE INVENTION

Figure 1:
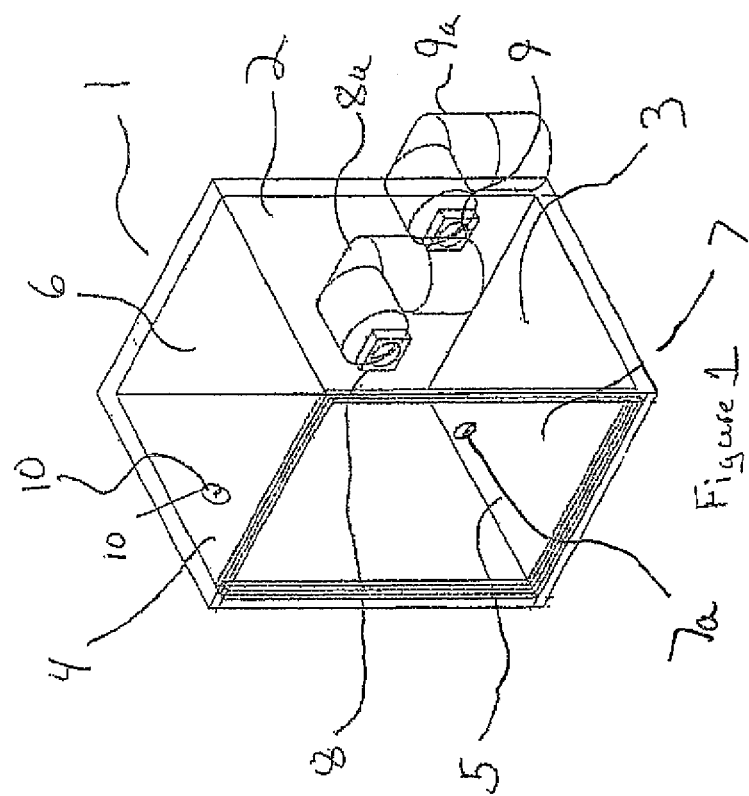
FIG. 1 is a transparent front view of an embodiment of the receptacle of the present invention.
Figure 2:
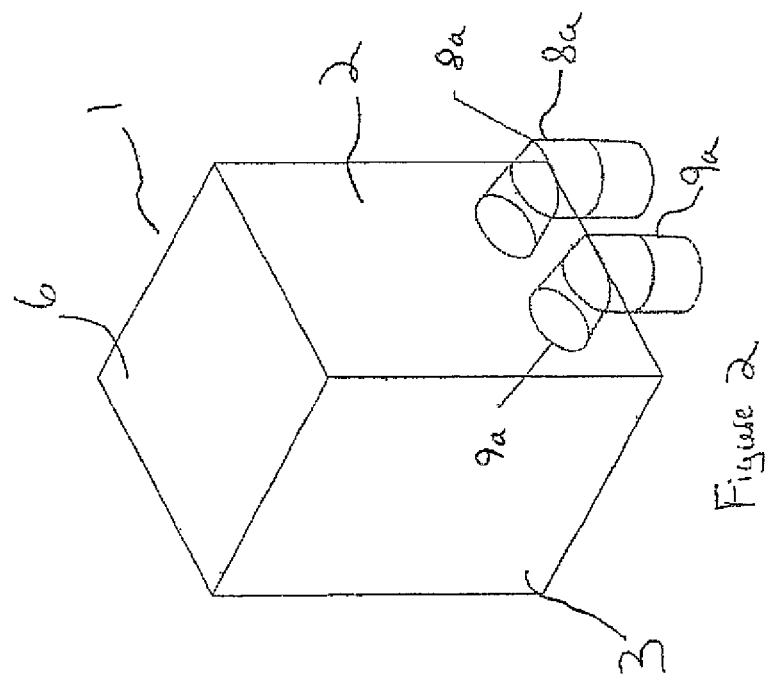
FIG. 2 is a rear view of the receptacle of FIG. 1.

Examples of the receptacle 1 of the present invention are shown in the attached figures. FIGS. 1-2 show a first embodiment of the receptacle 1 of which FIG. 1 is a front view and FIG. 2 is a rear view. The receptacle has a rear sidewall 2 and a first 3 and second sidewall 4 that are oppositely situated and that extend from the rear sidewall 2 to the front of the receptacle. A bottom wall 5 is positioned at the bottom of the sidewalls and a cover 6 is positioned on the top of the sidewalls. The bottom wall, top wall, and sidewalls combine to form a five walled rectangular receptacle that has an opening in the front for receiving a sealable door 7 that may be hinged to a sidewall of the receptacle by any means known in the art and that further includes a handle portion 7a. The handle portion may have a latch mechanism that enables the door to be locked in a closed position. In addition, the edges of the door 7 and the edges of the walls of the receptacle that contact the door are preferably equipped with means that enable the door to seal the receptacle when the door is in the closed position. These means may include but are not limited to an adhesive foam gasket that is applied to either the door or the unit to form an airtight seal. Alternatively, a rubber coating on the edges of the door and/or the edges of the walls that come into contact with the door's edges may be employed. Further, any other means for sealing an enclosure may also be used. The sealing feature of the door 7 prevents the escape of any contaminants from the firefighter turnout gear.

An intake fan 8 to provide fresh air to the enclosure and an exhaust fan 9 to remove stale air from the enclosure formed by the walls of the receptacle may be positioned on the rear wall of the receptacle but other locations on the receptacle are allowable. The intake S and exhaust 9 fans may be secured to the receptacle by screws or by any other adhesion or connecting mechanism known in the art and each fan is in fluid communication with the inside area of the receptacle by, for example, one or more orifices in one or more sidewalls of the receptacle. Further, the intake 8 and exhaust fans 9 preferably have a sealable connection with the receptacle to prevent the escape of any contaminated air from the inside of receptacle except through the orifices in communication with the fans. The sealable nature of the connection may be obtained by any means known in the art, such as but not limited to an adhesive foam gasket or a sealant tape or means that provides a sealed connection between the fans and the receptacle.

In an embodiment, the intake and/or exhaust fan may each be placed in a casing that each may be received by a corresponding orifice in at least one of the sidewalls of the receptacle. The casing may have a portion that is situated in the interior of the receptacle and/or a portion that is situated on the exterior of the receptacle in contact with interior and/or exterior sidewall surface, respectively. The interior and exterior portions have an orifice that allows the fan to be in fluid communication with the inside of the receptacle. The orifice of one or both of the portions may be smaller, substantially equal to, or larger than the orifice in the sidewall that receives the fan casing.

The portions in communication with the fan may help in providing the sealability for the intake and exhaust fans 8 and 9. They may have a sealing aid, such as adhesive foam gasket tape, other sealant tape, or other sealant aids known in the art. The casing and interior and exterior portions may be a single structure or may be separable parts such that they are connected by screws or other means known in the art. Further, the interior and exterior portions may be secured to the respective sidewall surfaces by screws, snap locks, a strong adhesive, or other known means in the art.

The intake and exhaust fan 8 and 9 casings may also include at least one air filter in fluid communication with the fan. The filter may be removable and cleaned or disposable and replaced. The filtering means may be located in the respective sidewall orifice and be situated between the fan and the inside of the receptacle. Alternatively or additionally, there may be a filtering means that may be situated in the orifice and located between the fan and the respective ducts.

A fan motor may be located in the casing, interior or exterior sidewall surface portions or other desired locations on the receptacle. The motor may be battery powered or may be powered by a power cord that may be adapted to plug into electrical outlets in a house or vehicle. Further, the battery powered feature of the fan may include removable or non-removable batteries and/or rechargeable or non-rechargeable batteries. At least one switch may also be used to operate the fan motors. There may be a separate switch for the exhaust and intake motors or there may be one switch that operates both fan motors, such that the intake and exhaust fans are either on or off at the same time. The switch may be located anywhere on the sidewalls of the receptacle or on the casing or any portions of the receptacle. The switch may be of any known in the art, such as a toggle switch or a push button switch. Further, the fan motors may be adapted to be operable via a remote control. The remote control may have a timer feature and/or sleep feature to allow a user to set desired times for the fans to operate to ventilate the receptacle.

In addition, rather than a user determining the operation of the fans, there may be at least one sensor in the receptacle's enclosure that determines when the enclosure needs to be ventilated. Here, if the sensor senses that the receptacle needs to be ventilated, the sensor may send a signal to the power source of one or all of the fan motors to turn on one or more of the fans. When it is sensed that ventilation can stop, the sensor may send a signal to the fan motors to turn off the fans that were operating. An example of a sensor may be but is not limited to an ionization smoke detector, a photoelectric smoke detector or one ionization smoke detector and one photoelectric smoke detector. The ionization smoke detector and/or photoelectric smoke detector may detect the presence of smoke or other particles in the receptacle and transmit a signal to one or more of the fans to turn on. When the smoke or other particles cease to be detected, the detectors may transmit a signal to turn off the fans.

A cleaning means may also be included in the receptacle's enclosure to sanitize and/or sterilize the items in the enclosure. This means may include but is not limited to a UV light source that may be operable by a switch or remote as has been described herein for the intake and exhaust fans. The UV light source may also include a timer and/or a sleep feature. Further, the UV light source may be battery powered as described herein or may be powered by a power cord plugged into an electrical outlet of, for example, a house or a vehicle. The UV light source may be on when the intake and exhaust are also on.

Also included in the ventilation means of the present invention may be ducts 8a and 9a connected to the intake fan and exhaust fan, respectively, to be in fluid communication therewith. The ducts 8a and 9a are preferably sealed around the intake and exhaust fan, respectively, to prevent any incoming or outgoing air from escaping the ducts. The ducts may be in fluid communication with the fans 8 and 9 through telescopic means such that the duct may fit snugly inside at least the orifice in the exterior portion such that it may be secured by a friction fit means. There may also be a sealant aid around the portions of the duct that are in contact with the surface of the portion's orifice to prevent the flow of air through any portions other than the ducts.

The ducts of the present invention extend to a safe location to receive air that is to be delivered to the enclosure and to exhaust air that is to be removed from the enclosure. When the receptacle of the present invention is stored in a vehicle, living quarters or other similar setting, the intake and/or exhaust duct 8a and 9a preferably extend to an area that is outside of the vehicle or living quarters so that the inside of the receptacle can be safely ventilated.

In an embodiment of the invention when the receptacle is positioned in a cabinet that is located in the trunk of a vehicle, the intake and exhaust ducts may extend to a location that is outside of the vehicle. In addition, the intake and exhaust ducts preferably extend to a different location so that the contaminated air leaving the exhaust duct does not enter the intake duct. For example, the intake duct may be in fluid communication with the outside of the front of a vehicle and the exhaust duct may be in fluid communication with the outside of the rear of the vehicle. In particular, the intake duct may extend to a location that is at the outside or in fluid communication with the outside of the front of the vehicle and the exhaust duct may extend to a location that is at the outside or in fluid communication with the outside of the rear of the vehicle. In this embodiment, the vehicle may include modifications to allow the ductwork to extend to different locations in the vehicle. For example, one or both of the ducts may be in the form of piping. The intake duct may extend from the receptacle and extend through an orifice in the floor of the trunk of the vehicle. The duct may then extend along the chassis of the vehicle from the rear of the vehicle to be in fluid communication with a point on the front of the vehicle, such as the vehicle grill. The duct may be secured to the chassis by brackets that may be connected to the chassis via screws or other means. Further, other means used in the art to secure piping to a vehicle frame, body, and/or chassis may also be used. The duct may extend to the front grill to receive air that is being displaced when the vehicle is moving in a forward direction or the duct may remain along the chassis and almost resemble a muffler in the front of the vehicle that will also receive air being displaced when the vehicle is moving in a forward direction.

The exhaust duct may be in the form of piping that extends through an orifice in the floor of the trunk. The piping may extend along the chassis to the rear of the vehicle where it is preferably in fluid communication with the rear of the vehicle. In one embodiment the exhaust duct may resemble an extra muffler-like appearance on the rear of the vehicle. Similar to the intake duct, the exhaust duct may be secured to the chassis by bracket means or other means used in the art to secure piping to a vehicle frame, body, and/or chassis.

In the arrangement of the receptacle being located in the trunk of a vehicle where the ducts resemble piping extending through the vehicle, a fan may not be required because air being displaced by the car being driven in a forward direction may enter the intake duct and force air out of the receptacle via the exhaust duct. The airflow in this example will be from the front of the vehicle to the rear of the vehicle to ventilate the receptacle. A check valve or other flow restrictor used in the art may be positioned at one or both openings of the receptacle that is connected to the ducts to ensure that the contaminated air does not flow from the receptacle to the intake duct and/or from the exhaust duct to the receptacle, such as when the vehicle is driven in reverse. It will be appreciated by those skilled in the art that the intake and/or exhaust ducts may extend to any other locations that are outside of the vehicle. In addition it will also be appreciated by those skilled in the art that there may be more than one intake and/or exhaust ducts connected to the receptacle and that the receptacle may have at least one opening connected to the at least one exhaust duct and/or intake duct, respectively.

In further embodiments of the receptacle being located in the vehicle, the intake and exhaust means may include intake and exhaust fans and their respective ducts being placed in different locations than shown in the Figures. For example, the intake and extending duct may be located on the rear sidewall and extend to a distal open end at a point on the vehicle that is in fluid communication with the outside of the vehicle. Further, the exhaust fan and extending duct may be located on the bottom wall of the receptacle and extend to a distal open end to the bottom of the vehicle, as has been described herein, to remove air from the enclosure at a location that does not contaminate the intake duct. Here and in all other embodiments, the distal open ends of the ducts may have covers to cover the ducts when the receptacle is not in use or is not desired to be ventilated. Having the intake fans and exhaust fans in the receptacles that are placed in the vehicles allows a user to ventilate the receptacle while the vehicle is not being driven. There may be a communication between the fans and the distal duct covers that causes the covers to open when the fans are turned on and operating.

Further, the fans may also aid in the ventilation while driving and while the duct caps are off. Here, the rush of air through the ducts may cause the fan blades to spin to further enhance the circulation of air through the enclosed area of the receptacle.

There may be more than one receptacle in a vehicle, more than one cabinet with a receptacle in a vehicle, or more than one exhaust and/or intake ducts extending from a receptacle from one or more orifices of the receptacle. The respective intake ducts may converge or remain singular and extend to a point that is in fluid communication with the front of the vehicle. Similarly, the respective exhaust ducts may converge or remain singular and extend to a point that is in fluid communication with the rear of the vehicle.

In further embodiments of the invention, it is also contemplated that the inside of the receptacle may be in communication with a fan to circulate air inside of the receptacle. In these embodiments, the fan may be preferably located inside of the receptacle to prevent smoke and other contaminants inside of the receptacle from settling or collecting on the surfaces therein.

At least one hook 10 may be placed on the inside of second sidewall 4 of the enclosure for hanging an item such as a firefighter protective coat and trousers. In other embodiments, the at least one hook may be placed on any other wall of the enclosure which includes the sealable door. The hooks may be secured to a surface on the inside of the receptacle by any means used in the relevant art, such as by screws, by an adhesive on the back of the hook, by a Velcro hook and loop fastening system, etc.

With reference now to FIGS. 3a-3b, shown in FIG. 3a is the receptacle of FIG. 2 and shown in FIG. 3b is a cabinet that includes the receptacle of FIG. 3a wherein the cabinet includes the receptacle 1 and an additional storage area 11 that is uncovered. The uncovered storage area 11 is preferably used to store firefighter items that are not required to be stored in a protective case. Such items may include a self-contained breathing apparatus ("SCBA") bottle and other tools and items not required to be stored in a protective casing. The storage area 11 as shown in FIG. 3b includes a bottom wall 12, a rear sidewall 13 and a sidewall 14 extending from the rear wall 13 to the front of the storage area 11. The rear sidewall 13 is preferably an extension of the rear sidewall 2 of the receptacle 1 but it may be a separate wall that extends from the exterior surface of the receptacle's second sidewall 4. In addition, in the embodiment shown in FIG. 3*b*, the exterior of the receptacle's second sidewall 4 functions as an additional sidewall for the storage area 11 so that the storage area has 3 sidewalls with an open front. Alternatively, rather than the exterior of the second sidewall 4 serving as the additional sidewall, the additional sidewall may include a separable wall that extends from the rear wall 13 to the front of the storage area and that lies flush against the receptacle's second sidewall.

The storage area may further include a slidably received drawer 15 situated atop the bottom wall 12 of the storage area. The drawer 15 may include a bottom wall 16 that has a first sidewall 17 and a second sidewall 18. Also included in the drawer may be a SCBA bottle retaining assembly 19 that is centrally located on a first side surface of the bottom wall 16. The retaining assembly 19 may include an L-shaped SCBA bottle support member 20 and a SCBA bottle retaining member 21 secured to the bottle support member. The SCBA bottle support member 20 further comprises a base 20*a* that extends perpendicularly from the bottom of an elongate body portion 20*b*. The SCBA retaining member 21 is preferably in the form of a strap but it may be any other type of retaining member used in the art, such as but not limited to a bracket. The storage area 11 further includes a shelf 22 to accommodate the storage of additional items. A non-slip material 23 may coat the side of the shelf that receives items to be stored thereon.

In operation, the drawer 15 may slide out of the storage area 11 and the bottle support member 20 may be pivoted from a bottle storage position as depicted in the figures to a bottle loading position such that the base 20*a* of the support member 20 extends parallel to the bottom wall 16 of the drawer 15 while the body 20*b* of the support member 20 extends perpendicular to the bottom wall 16 of the drawer 15. In the bottle storage position that is shown in the figures, the base 20*a* extends perpendicularly in relation to the bottom wall 16 of the drawer 15 while the body 20*b* of the support member 20 rests on the first side surface of the drawer's bottom wall 16.

In operation, the base of the SCBA bottle is placed on the support member 20 so that the bottom surface of the tank is in contact with the top surface of the support member's base 20*a* while the side of the tank is in contact with the support member's elongate body 20*b*. The retaining member strap 21 may then be wrapped around the side of the bottle to restrain its movement. It will be appreciated by those skilled in the art that the present invention allows for more than one retaining member to be used in further alternate embodiments and that items other than bottles may be stored in the retaining assembly.

Figure 4:
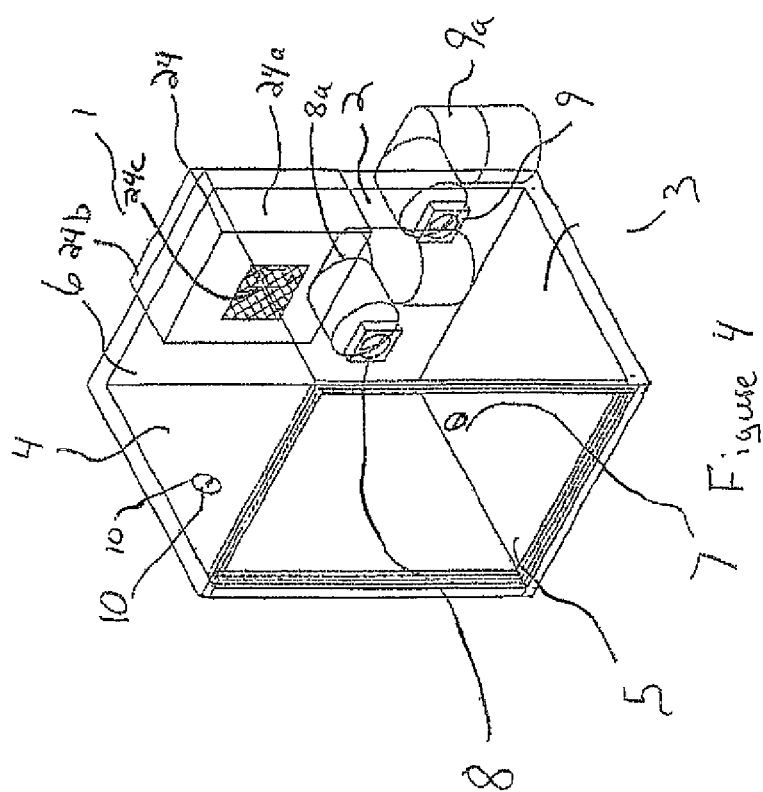
FIG. 4 is a transparent front view of an alternate embodiment of the receptacle.
Figure 5:
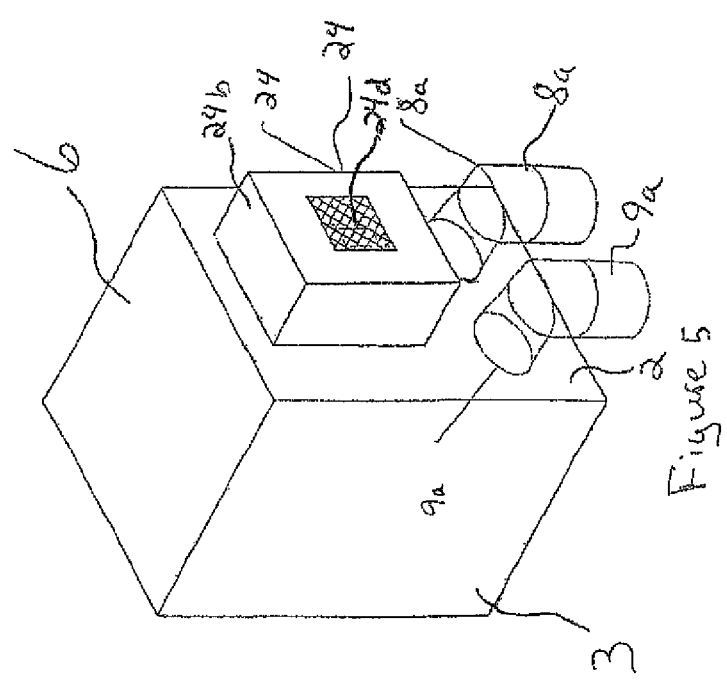
FIG. 5 is a rear view of the receptacle of FIG. 4.

A further alternate embodiment of the receptacle 1 is shown in FIGS. 4-5. FIGS. 4-5 show the receptacle 1 as further including a temperature control unit 24 that is mounted on the rear wall 2 of the receptacle 1. The temperature control 24 unit may be mounted on the rear wall 2 to preferably have a portion of the temperature control unit 24*a* extending into the inside of the receptacle and a portion 24*b* that extends outside of the receptacle 1. The temperature control unit 24 is preferably in the form of a rectangular housing that may have a vent 24*c* for controlling the temperature inside of the receptacle and a vent 24*d* for expelling exhaust from the temperature control unit. There may also be a filter in fluid communication with the temperature control unit to filter air entering and leaving the unit.

The temperature control unit may be powered by an electrical cord that may be adapted to be plugged into a house or car electrical source. Alternatively, the unit may be battery powered by removable or non-removable batteries that may be rechargeable or non-rechargeable.

There is preferably a sealant around the contact point between the edges of the temperature control unit and the rear wall of the receptacle so that no contaminants can escape therethrough. The sealant may be of the type disclosed in this application. It will be appreciated by those skilled in the art that the temperature control unit can be placed on any of the receptacle's other walls and that there may be separate units for heating and cooling the enclosure rather than one singular unit as shown in the Figures.

Shown in FIGS. 6*a*-6*b* is that the receptacle of FIGS. 4-5 can be included in a cabinet. FIG. 6*a* is a view of the receptacle of FIG. 4. FIG. 6*b* is a view of the receptacle of FIG. 6*a* that is included in a cabinet.

FIGS. 7-8 depict an even further alternate embodiment of the receptacle of the present invention. The receptacle of this embodiment is substantially the same as the receptacle of FIGS. 1-2, except this embodiment includes at least one removable or non-removable shelf 25 inside of the receptacle that provides additional storage means. The shelf spans the length and width of the inside of the receptacle but other sizes are also contemplated. In addition, more than one shelf may be placed in the receptacle. The shelf may be supported in the receptacle by ordinarily used means, such as but not limited to resting on shelf support pins or pegs that are inserted into the receptacle's sidewalls. Not shown in this embodiment is the receptacle including a hook on one of its sidewalls, however, it is contemplated that one or more hooks or other hanging means may be included on one or more sidewalls of the receptacles and/or on the bottom surface of the shelf 25.

Shown in FIG. 8 is a cabinet that includes the receptacle of FIG. 7 wherein the receptacle includes a base 26 that has an opening for receiving a drawer 27 wherein the drawer may contain a ratcheting command board with a whiteboard and/or other desired items. The command board may be powered with the means that have been described herein for the temperature control unit and the intake and exhaust fans. Further, the command board may also have communication capability, such as but not limited to telecommunication capability.

The drawer 27 further includes handles 28 on its front wall 29 to open and close the drawer. The rear, first, and second sidewalls 2, 3, and 4 of the receptacle 1 extend from the receptacle's top wall 6 to a bottom wall 30 of the opening that receives the drawer 27. As a result, the rear sidewall 2, first sidewall 3, and second sidewall 4 of the receptacle are also the rear sidewall, first sidewall and second sidewall of the opening. The bottom wall 5 of the receptacle, which is secured to the rear, first, and second sidewalls 2, 3, and 4 of the receptacle, forms the top wall for the opening.

A storage area 31 is also coupled to the receptacle 1 in FIG. 8. The storage area is bound on one side by the exterior surface of the receptacle's second sidewall 4 that extends from a bottom wall 32 of the storage area 31. The storage area 31 also has a rear wall 33 that extends from the bottom wall 32 and the exterior surface of the receptacle's second sidewall 4. The rear sidewall 33 is preferably an extension of the rear sidewall 2 of the receptacle 1 but it may be a separate wall that extends from the exterior surface of the receptacle's second sidewall 4. In addition, rather than the exterior surface of the receptacle's second sidewall 4 serving as a border for the storage area, a separate wall may be used.

The storage area, in other embodiments may have more or less sidewalls than shown in FIG. 8 and it may have a top wall.

The storage area 31 also includes a SCBA bottle retaining assembly 34, the top of which is shown in FIG. 8. The retaining assembly 34 preferably includes a bottle support member 35 and a bottle retaining member 36. The bottle support member 35 includes an elongate body portion 35a that is secured to and preferably extends from an upper portion of the rear sidewall to the bottom of the rear sidewall (not shown). The bottle support member may also include a base (not shown) that is secured to and extends from the bottom of the elongate body portion 35a. The base may be secured to and extend along a portion of the bottom wall 32 of the storage area. The base is preferably of the type that is shown in FIG. 3b such that the base and elongate body portion 35a combine to form an L-shaped bottle support member that is centrally located along the rear 33 and bottom wall 32 of the storage area 31. The bottle retaining member 36 is shown as secured to the top portion of the bottle support member's body portion 35a. The retaining member is preferably a ring shaped bracket in this embodiment that has a first end 36a and a second end 36b that have a space therebetween that is opposite the retaining member's connection with the support member's body portion.

FIGS. 9-10 show the receptacle of FIGS. 7-8 as further including a temperature control unit 24 mounted to the rear wall 2 of the receptacle. The temperature control unit 24 in this embodiment is preferably in line with the rear sidewall 2 of the receptacle 1, meaning that it does not have a portion extending into the inside of the receptacle as in the receptacle of FIG. 4. FIG. 9 shows the receptacle by itself while FIG. 10 shows the receptacle as coupled to the cabinet that is shown in FIG. 8.

The embodiments of the receptacle in FIGS. 1-6b show a long rectangular shaped receptacle whereas the embodiments of the receptacle in FIGS. 7-10 show a boxier rectangular shaped receptacle. Other shapes, however, are also contemplated such as but not limited to a square, a circle, etc.

In even further embodiments of the invention, more than one receptacle may be coupled to a cabinet and/or the cabinet may include additional drawers and/or storage areas. The cabinets and receptacles are preferably made of a metal, such as aluminum, but other materials used in the relevant art are also contemplated. In addition, the interior surfaces of all or some of the walls of the storage area, receptacle, and/or drawers may be lined with carpeting.

What is claimed is:

1. A receptacle configured to store firefighter turnout gear in a body of a vehicle, said receptacle comprising; a bottom wall, at least one side wall extending from said bottom wall to a top wall to define an enclosed area, a door hinged to at least a portion: of said side wall, being configured to occupy an open position to allow access to said enclosed area, and configured to occupy a closed position; means for sealing said door when in said closed position to form an air-tight enclosure with respect to an interior of the vehicle; and a system for ventilating said enclosure with respect to the exterior of the vehicle, said ventilation system configured to provide air into said enclosure and to remove air from said enclosure to ventilate the firefighter turnout gear stored in said enclosure; wherein said ventilation system comprises an intake duct extending from said receptacle, being in fluid communication with the outside of the vehicle to provide air into said enclosure, and an exhaust duct extending from said receptacle at a different point than said intake duct, being in fluid communication with the outside of the vehicle at a different location than said intake duct; at least one hook secured to said sidewall inside said enclosure, being configured to hang a protective coat and trousers of the firefighter turnout gear; wherein said receptacle is coupled to a storage area, said storage area configured for the storage of items outside of said receptacle; said receptacle further comprising a drawer slidably coupled to an exterior portion of said receptacle, said-drawer configured to slide from a retracted position to an extended position to expose an interior of said drawer; said drawer comprising: a bottle support member configured to receive and support a fire fighter self-contained breathing apparatus therein, said bottle support member configured to be pivoted from a bottle storage position to a bottle loading position; said drawer comprising a retaining strap configured to restrain movement of the fire fighter self-contained breathing apparatus.

2. The receptacle according to claim 1 wherein said drawer comprising a ratcheting command board.

3. The receptacle according to claim 2 wherein said ratcheting command board is configured to be powered by an electrical cord configured to be plugged into an electrical source of the vehicle.

4. The receptacle according to claim 2 wherein said ratcheting command board comprises a communication capability.

5. The receptacle according to claim 2 wherein said drawer further comprises a whiteboard.

6. The receptacle according to claim 1 further comprising at least one shelf positioned inside of said enclosure.

7. The receptacle according to claim 1 wherein said ventilation system comprises at least one intake fan secured to at least a portion of said sidewall; at least one exhaust fan secured to at least a portion of said sidewall that is different from said intake fan; and at least one sensor in said enclosure, said sensor configured to detect smoke in said enclosure, and to turn on said fans when smoke is detected, and turn off said fans when smoke is no longer detected.

8. The receptacle according to claim 7 wherein said intake duct is in fluid communication with said intake fan.

9. The receptacle according to claim 8 wherein said exhaust duct is in fluid communication with said exhaust fan.

10. The receptacle according to claim 9 wherein said receptacle further comprises a temperature control unit mounted in said enclosure, said temperature control unit configured to control a temperature within said enclosure.

11. The receptacle according to claim 9 wherein said intake duct extends to an area that is in fluid communication with the front of the vehicle.

12. The receptacle according to claim 11 wherein said exhaust duct extends to an area that is in fluid communication with the rear of the vehicle.

13. The receptacle according to claim 12 wherein a flow restrictor is positioned along at least a portion of said intake and/or exhaust ducts, said flow restrictor permitting the flow of air into and restricting the flow of air out of said receptacle when said flow restrictor is positioned along at least a portion of said intake duct and said flow restrictor restricting the flow of air into and permitting the flow of air out of said receptacle when said flow restrictor is positioned along at least a portion of said exhaust duct.

14. The receptacle according to claim 13 wherein a portion of air being displaced from the vehicle moving in a forward direction enters said intake duct, said air flowing from said intake duct into said enclosure and out of said enclosure through said exhaust duct to the outside of the vehicle to ventilate said enclosure.

15. The receptacle according to claim 7 comprising a fan configured to circulate air within said enclosure.

16. The receptacle according to claim 15 comprising a filter configured to filter the air into and the air out of said enclosure.

\* \* \* \* \*